(12) United States Patent
Yiu et al.

(10) Patent No.: US 6,242,924 B1
(45) Date of Patent: Jun. 5, 2001

(54) METHOD FOR ELECTRONICALLY MEASURING SIZE OF INTERNAL VOID IN ELECTRICALLY CONDUCTIVE LEAD

(75) Inventors: Tsui Ting Yiu, Palo Alto; Yow Juang W. Liu, San Jose; Young-Chang Joo, Sunnyvale; Sunil N. Shabde, Cupertino, all of CA (US)

(73) Assignee: Advanced Micro Devices, Sunnyvale, CA (US)

( * ) Notice: Subject to any disclaimer, the term of this patent is extended or adjusted under 35 U.S.C. 154(b) by 0 days.

(21) Appl. No.: 09/236,844

(22) Filed: Jan. 25, 1999

(51) Int. Cl.[7] .......................... H01H 31/02; G01R 31/08
(52) U.S. Cl. ........................................ 324/543; 324/525
(58) Field of Search ........................... 324/543, 525, 324/707

(56) References Cited

U.S. PATENT DOCUMENTS

| | | |
|---|---|---|
| 3,693,074 | 9/1972 | Holler et al. . |
| 3,808,527 | 4/1974 | Thomas . |
| 4,564,810 | 1/1986 | Geithman et al. . |
| 5,202,641 | 4/1993 | Unvala . |
| 5,214,389 | 5/1993 | Cao et al. . |
| 5,293,119 | 3/1994 | Podney . |
| 5,400,209 | 3/1995 | Moslehi . |
| 5,418,459 | 5/1995 | You et al. . |
| 5,473,248 | 12/1995 | Haldemann et al. . |
| 5,585,734 | 12/1996 | Meuris et al. . |
| 5,691,644 | * 11/1997 | Danilyak ............... 324/543 |
| 5,963,031 | 10/1999 | de Halleux et al. . |

OTHER PUBLICATIONS

Sadiku, Elements of Electromagnetics, 1995 Second Edition, pp. 470–471, Oxford University Press, Inc., New York, New York, US.

* cited by examiner

*Primary Examiner*—Safet Metjahic
*Assistant Examiner*—J Kerveros
(74) *Attorney, Agent, or Firm*—David G. Alexander; Arter & Hadden LLP

(57) ABSTRACT

The size of an internal void in an electrically conductive lead is measured by determining its electrical resistance at a plurality of A.C. frequencies, ranging from D.C. to a frequency on the order of 50 to 100 GHz at which the majority of current flows along the skin of the lead. The test data is compared with reference data for an electrically conductive reference lead having characteristics which are essentially similar to the test lead. The difference between the two sets of data increases with the size of an internal void in the test lead. The difference will be greatest at D.C. because the current will flow through substantially the entire cross-section of the lead and the cross-sectional area will be reduced by the internal void. The test data will approach the reference data as the frequency increases because the majority of the current will flow through the skin of the test lead and will be less affected by the internal void. The surface roughness of a lead caused by surface voids is measured by determining its electrical resistance at a frequency high enough that the majority of the current flows through the skin of the lead. The distance at which the surface current flows, and thereby the resistance of the lead, increase with the surface roughness.

5 Claims, 1 Drawing Sheet

METHOD FOR ELECTRONICALLY MEASURING SIZE OF INTERNAL VOID IN ELECTRICALLY CONDUCTIVE LEAD

BACKGROUND OF THE INVENTION

1. Field of the Invention

The present invention generally relates to the art of microelectronic integrated circuits, and more specifically to a method for measuring the surface roughness and size of an internal void in an electrically conductive lead in the metallization pattern of an integrated circuit chip.

2. Description of the Related Art

Microelectronic integrated circuit chips include large numbers of microelectronic devices which are interconnected by one or more layers of metallization. Each layer consists of an intricate pattern of electrically conductive leads made of copper, tungsten, aluminum, etc. Some of the leads can be quite long relative to the overall size of the circuit.

The leads are typically formed by depositing a metal layer on a dielectric layer of the chip, depositing a photoresist layer on the metal layer, photolithographically patterning the photoresist layer to form a mask having openings in which metallization is not desired, and then etching away the exposed metal through the openings in the mask. The photoresist mask is then dissolved away to leave the desired metallization pattern of electrically conductive leads.

The process for forming the metallization layers includes a number of critical variables, and it, as well as subsequent processing steps if not performed with requisite precision, can result in imperfections in the conductive leads. These imperfections are generally of two types, external or surface voids on the surface of a lead, and internal voids within the material of the lead.

As illustrated in FIG. 1, an electrically conductive lead 10 has a generally rectangular cross-section, and can have an internal void 12 as a result of imperfect fabrication processing. The lead 10 can also have external or surface voids on its surface. As designated by the reference numeral 14a, surface voids can be small, and extend along only a small portion of the width of the lead 10. The voids can also be larger as indicated at 14b, or extend along the entire width of the lead 10 as indicated at 14c.

Surface voids 14a, 14b and 14c generally have an iso-triangular cross section (the shape of an isosceles triangle) as illustrated at 16 in FIG. 2, and can be relatively shallow or deep. The surface roughness of a lead is determined by the number and sizes of surface voids. Internal voids are also known as "seams", and can also have varied sizes.

Surface roughness of conductive leads due to surface voids has a highly detrimental effect on the electrical performance of an integrated circuit chip, especially with long leads at high frequencies. Surface roughness increases the distance that electrical signals have to travel, thereby creating timing delays and inconsistencies.

Surface roughness also increases the electrical resistance of leads, requiring higher voltages to ensure reliable signal transmission. In extreme cases, many large voids can cause a failure of the circuit to function properly.

Internal voids are also highly detrimental, especially at D.C. or low frequencies. As with external voids, internal voids increase the electrical resistance of the leads and require higher voltages for reliable operation.

Fabrication of integrated circuit chips requires constant monitoring of quality throughout many process steps to ensure that time and expense are not wasted by additionally processing chips that are already defective. A method for monitoring the size and growth of voids in conductive leads as the fabrication processing proceeds is a highly desirable capability for quality control. However, a satisfactory method for achieving this goal has not been heretofore proposed in the art.

SUMMARY OF THE INVENTION

The present invention fills a need which has heretofore existed in the art, and provides a method for monitoring the size and growth of internal and external voids in an electrically conductive lead on a microelectronic integrated circuit chip.

More specifically, the size of an internal void in an electrically conductive lead is measured by determining its electrical resistance at a plurality of A.C. frequencies, ranging from D.C. to a frequency on the order of 50 to 100 GHz at which the majority of current flows along the skin of the lead. The test data is compared with reference data for an electrically conductive reference lead having characteristics which are essentially similar to the test lead.

The difference between the two sets of data increases with the size of an internal void in the test lead. The difference will be greatest at D.C. because the current will flow through substantially the entire cross-section of the lead and the cross-sectional area will be reduced by the internal void. The test data will approach the reference data as the frequency increases because the majority of the current will flow through the skin of the test lead and be less affected by the internal void.

The surface roughness of a lead caused by surface voids is measured by determining its electrical resistance at a frequency high enough that the majority of the current flows through the skin of the lead. The distance at which the surface current flows, and thereby the resistance of the lead, increase with the surface roughness.

These and other features and advantages of the present invention will be apparent to those skilled in the art from the following detailed description, taken together with the accompanying drawings, in which like reference numerals refer to like parts.

DETAILED DESCRIPTION OF THE INVENTION

Figure 1:
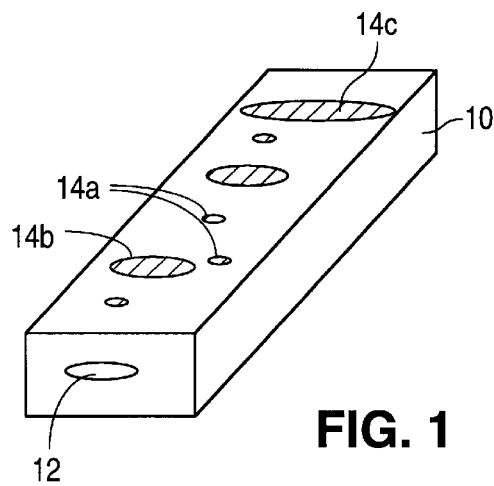
FIG. 1 is a simplified perspective view of an electrically conductive lead illustrating internal and external voids.
Figure 3:
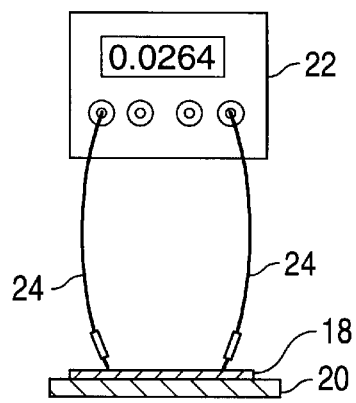
FIG. 3 is a simplified elevational view illustrating testing of a conductive lead in accordance with the present invention.

A method and apparatus for testing an electrically conductive lead in accordance with the present invention is illustrated in simplified form in FIG. 3.

As viewed in the figure, an electrically conductive lead 18 is formed on a microelectronic integrated circuit chip 20. An electrical ohm-meter 22 is constructed to measure electrical resistance at a plurality of A.C. frequencies from D.C. to, for example, 10 GHz.

The configuration of the ohm-meter 22 per se is not the particular subject matter of the invention and will not be described in detail. The ohm-meter 22 can be a commercially available unit. In general, the ohm-meter 22 will include a signal generator for generating an A.C. voltage at variable frequency, and metering circuitry for measuring the resulting current flow and calculating resistance as a function of voltage divided by current in accordance with Ohm's law.

The resistance of the lead 18 is measured by connecting the inputs of the ohm-meter 22 to the lead 18 at two longitudinally spaced locations using test probes 24. The measured resistance will increase with the distance between the probes 24 and thereby the length of the portion of the lead 18 under test. For this reason, a fixed distance is selected in accordance with the type of circuit and the size, material and electrical characteristics of the lead 18, and is used throughout the testing.

In accordance with the present method, tests are made to measure the surface roughness of the lead 18 due to surface voids, and to measure the sizes of internal voids. Both tests are performed using the ohm-meter 22 as illustrated in FIG. 3. It is preferable, but not necessary, to automate the testing using a digital computer under control of a suitable operating program.

Figure 2:
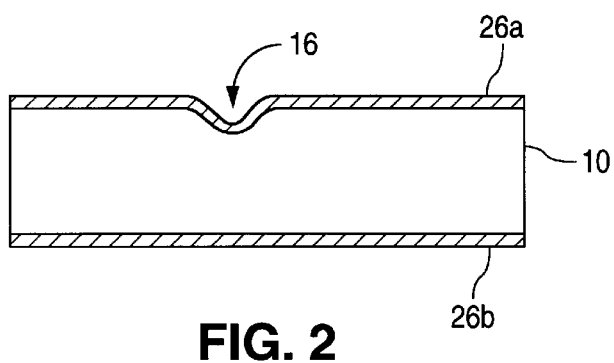
FIG. 2 is a simplified longitudinal sectional view of the lead showing a surface void.

The surface roughness is measured by applying an A.C. voltage to the lead 18 at a frequency which is sufficiently high that the majority of current flows through the surface or skin of the lead 18. This phenomenon is known as "skin effect". As illustrated in FIG. 2, the depth of the skin or the "skin depth" is a function of frequency. The skin of the lead 10 is designated as 26a at the top and 26b at the bottom in FIG. 2 and indicated by hatching.

The skin depth is defined as the distance from the surface at which the current density falls to 1/e of its value at the surface. The desired skin depth is selected mathematically or empirically in accordance with the size, shape, material and electrical characteristics of a particular lead being tested, and can vary considerably from one application to another.

Once the skin depth is selected, the frequency f to be used for testing is preferably calculated using the function:

$$f = \frac{1}{\pi \mu \gamma s^2}$$

where $\gamma$ is the resistivity, $\mu$ is the permeability, and s is the skin depth of the lead. However, it is not necessary to use the above equation to select the frequency, and this parameter can be determined empirically or by using any other applicable guideline.

As typical examples, for a copper lead, s is approximately 1.5 microns, and f is approximately 1.6 GHz. For a tungsten lead, s is approximately 2.5 microns and f is also approximately 1.6 GHz.

Figure 4:
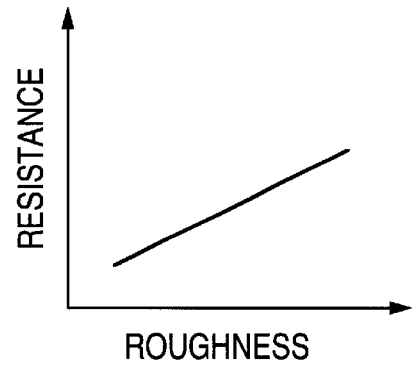
FIG. 4 is a graph illustrating measured electrical resistance as a function of surface roughness for a lead.

FIG. 4 illustrates how the measured electrical resistance varies as a function of surface roughness (number and size of surface voids). More specifically, the resistance $R \approx L/A$, where L is the distance that electrons have to travel along the skin of the lead, and A is the cross-sectional area of the skin. It will be noted that the skin depth decreases with frequency, and for this reason the tests are performed at a fixed frequency as described above.

As viewed in FIG. 2, the length L increases as the surface roughness increases. This is because the electrons have to flow a larger distance through the skin due to the presence of surface voids. The void 16 is formed in the upper surface of the lead 10.

The length of the skin 26a is therefore longer at the upper surface 26a than the length of the skin 26b in the lower surface of the lead which does not have a surface void. Since R L/A, the resistance is approximately proportional to the distance L as viewed in FIG. 4.

Therefore, the measured resistance is approximately proportional to the surface roughness, and the resistance constitutes an accurate measure thereof. The accuracy of the measurement is maximized by constraining the majority of the current to flow through the skin of the lead, because the increase of the distance L caused by voids is maximum at the surface.

Figure 5:
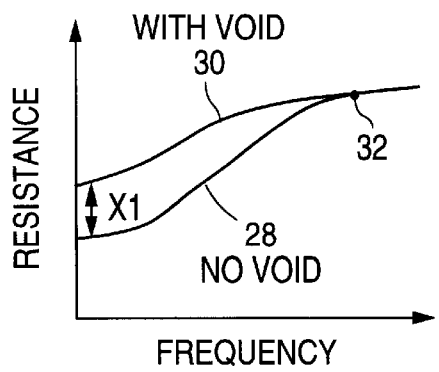
FIG. 5 is a graph illustrating measured resistance as a function of frequency for a lead having an internal void.
Figure 6:
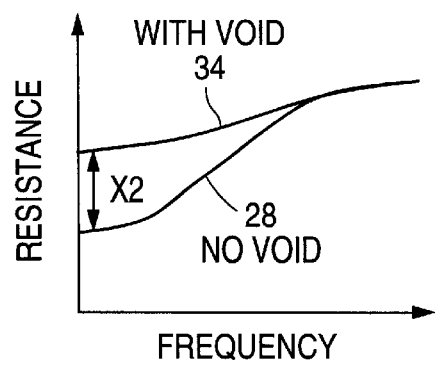
FIG. 6 is similar to FIG. 5, but illustrates data for a larger internal void.

FIGS. 5 and 6 illustrate the present method for measuring the size of an internal void or voids. In this case, reference data is preferably obtained by connecting the ohm-meter 22 to a reference lead having the same characteristics as a test lead which is to be tested. The reference lead is certified using any applicable method to have no internal voids, and preferably also to have no surface voids. The ohm-meter 22 applies an A.C. voltage to the lead 18 using the probes 24, and measures the resistance as described above.

The ohm-meter 22 ramps the frequency of the applied A.C. voltage between first and second values, preferably from zero (D.C.) to a high enough frequency that the majority of current flow will be through the skin of the lead. A preferred, but not limiting, upper frequency is 50 to 100 GHz. In connection with ramping up the frequency, the ohm-meter 22 measures the resistance at a plurality of values of frequency. The results can be plotted as a reference data curve 28 in FIGS. 5 and 6.

Although it is preferred that the reference data be obtained empirically, the invention is not so limited, and it is within the scope of the present method to obtain the reference data by mathematical calculation, previous experience, or from any other applicable source. It is, of course, further within the scope of the invention to ramp the frequency down rather than up, and to ramp the frequency between values other than zero and 50 to 100 GHz.

After the reference data has been obtained, a test lead is tested using the same procedure described above for the reference lead to obtain test data. If the test lead does not have any internal voids, the test data will be identical to the reference data, and both curves will appear as indicated at 28. However, if the test lead has one or more internal voids, the test data as indicated at 30 in FIG. 5 will be different from the reference data.

At very low frequency, current will flow through substantially the entire cross-section of the test lead. If the lead has an internal void, the cross-sectional area of the lead will be decreased. Since $R \approx L/A$, and in this case A is the entire cross-sectional area of the lead, the resistance is approximately inversely proportional to the area A. The area A can be expressed as $A = A_0 - A_v$, where $A_0$ is the entire cross-section of the lead and $A_v$ is the cross-sectional area of the internal void or voids. Since the presence of a void reduces the area A, the resistance R increases as the size (area) of the void increases as illustrated at 30 in FIG. 5.

As further shown in FIG. 5, the effect of an internal void is maximum at zero (D.C.) frequency, because the current flowing through the interior of the lead is affected by the void to a maximum extent. Thus, the test curve 30 is displaced upwardly from the reference curve 28 by a value X1 at zero frequency.

However, as the frequency is increased, the skin depth decreases and a progressively larger portion of the current flows through the skin and bypasses the internal void. At a sufficiently high frequency, substantially all of the current bypasses the void, and the test curve 30 merges with the reference curve as indicated at a point 32.

FIG. 6 is similar to FIG. 5, but illustrates the case of a larger internal void as indicated by a test curve 34 which is displaced from the reference 28 by a value X2 that is larger than the distance X1.

In summary, the present invention provides a method for monitoring the size and growth of internal and external voids in an electrically conductive lead on a microelectronic integrated circuit chip. The measurements are preferably performed at various appropriate stages in the fabrication process of an integrated chip on a number of leads. This enables the size and growth of internal and surface voids, if present, to be monitored accurately and quality control substantially enhanced.

Various modifications will become possible for those skilled in the art after receiving the teachings of the present disclosure without departing from the scope thereof.

What is claimed is:

1. A method for measuring a size of an internal void (12) in an electrically conductive lead (10), comprising the steps of:
   (a) obtaining reference data (28) including resistance as a function of frequency for an electrically conductive reference lead with no internal voids;
   (b) applying an A.C. voltage to an electrically conductive test lead (18) having characteristics which are essentially similar to the reference lead;
   (c) ramping a frequency of the A.C. voltage between a first value and a second value;
   (d) in connection with performing step (c), obtaining test data (30) by measuring resistance of the test lead (18) as a function of applied A.C. voltage and current at a plurality of frequencies; and
   (e) comparing the test data (30) with the reference data (28);
   whereby a difference between the test data (30) and the reference data (28) increases with a size of an internal void in the test lead (18);
   the first value in step (c) is sufficiently low that current flows through substantially an entire cross-section of the test lead (18); and
   the second value in step (c) is sufficiently high that a malority of the current flows through a skin of the test lead (18).

2. A method as in claim 1, in which step (a) comprises measuring resistance of an electrically conductive reference lead with no internal voids at a plurality of frequencies.

3. A method as in claim 1, in which one of the first and second values in step (c) is zero Hz.

4. A method as in claim 1, in which one of the first and second values in step (c) is 50 to 100 GHz.

5. A method as in claim 1, in which the first value is zero Hz and the second value is 50 to 100 GHz in step (c).

* * * * *